United States Patent
Chibata et al.

[11] 3,963,613
[45] June 15, 1976

[54] BLOOD PURIFICATION MEANS

[75] Inventors: Ichiro Chibata, Suita; Tetsuya Tosa, Kyoto; Takao Mori, Takatsuki, all of Japan

[73] Assignee: Tanabe Seiyaku Co., Ltd., Osaka, Japan

[22] Filed: Dec. 26, 1974

[21] Appl. No.: 536,641

[30] Foreign Application Priority Data
Dec. 29, 1973 Japan .................................. 49-608
Dec. 29, 1973 Japan .................................. 49-609

[52] U.S. Cl. .......................... 210/195 R; 128/214 R; 210/321 A; 210/321 B
[51] Int. Cl.² .................................... B01D 31/00
[58] Field of Search ............... 210/22, 23, 321, 195; 196/DIG. 11; 128/214 R

[56] References Cited
UNITED STATES PATENTS

| | | | |
|---|---|---|---|
| 3,619,423 | 11/1971 | Galletti et al. | 210/22 |
| 3,727,612 | 4/1973 | Sayers et al. | 210/22 X |
| 3,791,926 | 2/1974 | Chibata et al. | 195/DIG. 11 |
| 3,794,584 | 2/1974 | Kunin | 210/22 X |
| 3,809,613 | 5/1974 | Vieth et al. | 195/DIG. 11 |
| 3,839,200 | 10/1974 | Gigou et al. | 210/22 |
| 3,865,726 | 2/1975 | Chibata et al. | 210/321 X |

*Primary Examiner*—Frank A. Spear, Jr.
*Attorney, Agent, or Firm*—Wenderoth, Lind & Ponack

[57] ABSTRACT

A blood purification means whereby blood of a patient to be treated is led around an external circuit connecting to the patient's blood stream and is brought into direct or indirect contact with a fumarate solution, and is further brought into direct or indirect contact with an enzymic preparation, which is suitably an aspartase preparation, which catalyzes a reaction of L-aspartic acid formation from fumaric acid and ammonia. The purification means may further include a preliminary stage or stages whereat an unrequired substance in a patient's blood is decomposed to a non toxic substance and ammonia subsequently convertable to aspartic acid, and may also include a low molecular sieve means preventing re-entry of aspartic acid produced into the patient's blood stream.

2 Claims, 6 Drawing Figures

BLOOD PURIFICATION MEANS

BACKGROUND OF THE INVENTION

The present invention relates to a blood purification means employable in the treatment of patients for whom purification of blood by artificial means is necessary, for example sufferers from liver or kidney disorders, or leukemia. More particularly the invention relates to a blood purification means which is provided externally to a patient and is able to effect selective removal of an unrequired substance from the patient's blood stream.

In various known methods for medical treatment of maladies or disorders relating to blood there is employed means which are provided externally to, and are in arterial-venous, or less frequently, veno-venous connection to the blood stream of a patient to be treated, and which in effect constitute part of the circuit through which the patient's blood must flow, such means serving to effect pick-up by the patient's blood of a required substance, or purification of the patient's blood. For example, one use of such means is in treatment of liver disorder, in which treatment the purpose of the means is to remove from the blood of a patient ammonia which may be produced, at least partly as a result of medicaments with which the patient is treated, it being known to effect this removeal by conventional hemodialysis, or by passing the patient's blood through a purification bed of ion-exchange resin. However, such conventional means have the disadvantage that while ammonia is effectively removed, there is also removal of other substances which are preferably retained in the patient's blood. Similar problems are encountered in treatment of a patient for leukemia, for example, in which treatment it is known to remove asparagine from a patient's blood by employment of asparaginase, which is able to decompose asparagine to aspartic acid, which is non toxic to a living organism, and ammonia, which may be toxic even in very small quantity, and must therefore be subsequently removed. It is therefore a desideratum to provide a blood purification means which is able to effect selective removal of an unrequired substance such as ammonia from a patient's blood.

SUMMARY OF THE INVENTION

The present invention is in the field of blood purification means. More particularly the invention relates to a means for selective removal of an unrequired substance from the blood stream of a patient while allowing required substances to remain therein. The inventors, having taken note of the fact that ammonia incubated with fumaric acid can be converted by the action of aspartase into aspartic acid, which is non toxic, and the fact that asparagine is decomposed by the action of asparatinase to aspartic acid and ammonia, have provided a blood purification means according to one embodiment of which blood from a patient is led into an outflow cannula, which is in venous or arterial connection to the patient, into which fumarate solution is suppliable in controlled quantities, and which leads the blood and added fumarate solution into a unit which contains an enzymic preparation having a composition such that it may convert the fumaric acid and ammonia contained in the blood supplied along the outflow cannula to aspartic acid, if the purification means is used in treatment of a patient suffering from a liver disorder, for example, or such that it may convert asparagine contained in the blood supplied along the outflow cannula to aspartic acid and ammonia, and convert the ammonia thus produced and fumaric acid into aspartic acid, if the purification means is used in association with treatment of leukemia, blood thus cleaned of ammonia or other required substances being returned to the blood stream of the patient along an inflow cannula in arterial or venous connection thereto. The enzyme unit may be suitably constituted by an open ended cylinder connecting to the outflow cannula and inflow cannula and containing an enzymic preparation, which is retained by a membrane or a bonding lattice of semipermeable high molecular substance and is packed across the entire cross-section of the cylinder, or which is in the form of a tube. The enzymic preparation is suitably an aspartase preparation if the purpose is to eliminate ammonia, or an asparaginase and aspartase preparation if the purpose is to eliminate asparagine and subsequently produced ammonia. In the latter case the asparaginase preparation is suitably provided alone or mixed with the aspartase preparation at the inlet side of the enzyme unit connecting to the outflow cannula and the aspartase preparation at the outlet side of the enzyme unit.

According to another embodiment of the invention, blood from a patient is led into a hemodialysis unit in which the dialysate employed containes additions of fumarate and an aspartase preparation or of fumarate and a mixed asparaginase and aspartase preparation, whereby, simultaneously with normal dialysis of the patient's blood, there is effected conversion of ammonia into aspartic acid, or of asparagine into aspartic acid and ammonia, which is then converted to aspartic acid.

In a further embodiment of the invention, outflow and inflow cannulae lead to and from a conventional hemodialysis unit whose dialysate is constantly recirculated around a separate circuit including a dialyzer having a first compartment into and from which dialysate of the hemodialysis unit is transported and a second compartment which is separated from the first compartment by a semipermeable membrane permitting passage only of low molecular substances, and contains a dialysate to which additions of fumarate and aspartase preparation have been made. The dialysate of the hemodialysis unit is a conventional preparation of the purpose of the purification means is removal of ammonia from the patient's blood, and contains an addition of asparaginase preparation if the purpose is removal of asparagine. When blood enters the hemodialysis unit, ammonia diffuses into the dialysate thereof, or is formed therein by the action of the asparaginase preparation, and is then carried to the dialyzer where it diffuses into the dialyzer second compartment and is converted to aspartic acid, which is retained in the dialysate of the dialyzer since it cannot diffuse back through the low molecular substance semipermeable membrane.

DETAILED DESCRIPTION OF THE INVENTION

Figure 1:
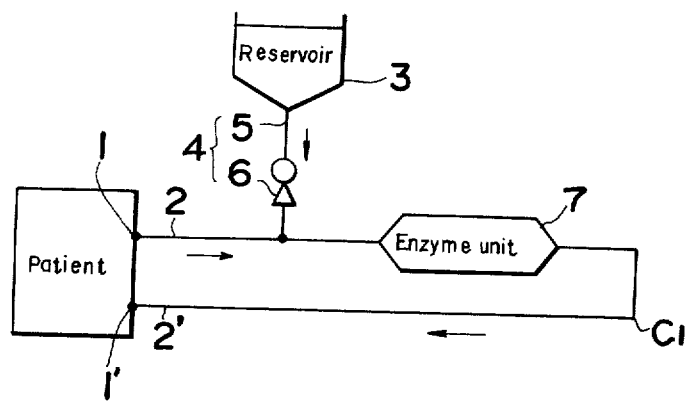
FIG. 1 is a schematic lay-out view of a blood purification means according to one embodiment of the invention.

Referring to FIG. 1, there is shown an outflow cannula 2 and an inflow cannula 2' which respectively lead into and from an enzyme unit 7, and have ends 1 and 1' which are adapted to be connected to the blood stream of a patient to be treated, connection being venous or arterial, and being direct or indirect, i.e., the ends 1 and 1' are adapted to be themselves directly connected to the patient's blood stream, or to be connected to shunt tubes which are left in permanent connection to the patient's blood stream. The cannulae 2 and 2' are suitably made of, for example, silicone rubber, teflon, polyethylene, or other such material not reactive to blood, and serve for transport of blood around a circuit C1, which leads from the patient, through the enzyme unit 7, and back to the patient, there being provided on the circuit C1 a conventionally known pump, not shown, if, as is most usual, arterial pressure is insufficient to maintain flow of blood around the circuit C1. Fumarate solution from a reservoir 3 may be supplied into the blood flowing in the outflow cannula 2 by a supply means comprising a tract 5, which connects the reservoir 3 to the outflow cannula 2, and is made of the same kind of material as the cannulae 2 and 2', and an adjustable flow pump, for example a peristaltic pump 6, which is provided on the tract 5 and controls supply of fumarate solution into the cannula 2. The fumarate in the solution in the reservoir 3 may be, for example, sodium fumarate or potassium fumarate, and the solution preferably also includes an addition of heparin or other suitable anticoagulant.

Figure 2:
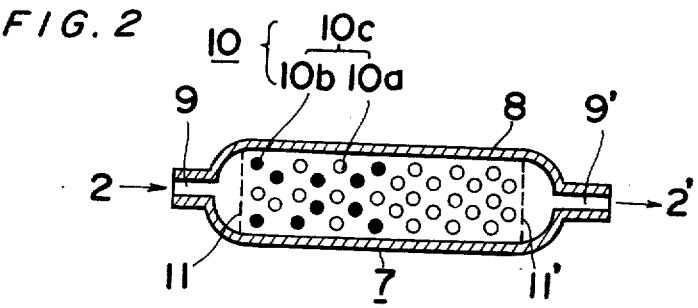
FIG. 2 is an enlarged cross-sectional view of an enzyme unit employed in the blood purification means of FIG. 1.

Referring to FIG. 2, the enzyme unit 7 comprises a column, generally cylindrical main portion 8, which is made of glass, a hard plastic such as polycarbonate, polyacrylate, or other suitable material that remains inert when in contact with blood, has opposite open ends 9 and 9' respectively connectable to the outflow cannula 2 and inflow cannula 2', and contains an enzymic preparation 10. The enzymic preparation 10 is constituted by grains or microcapsules which are retained in the main portion 8 by supporting membranes 11 and 11', which are made of nylon mesh or similar material, and extend completely across the internal section of the main portion 8, near opposite ends 9 and 9' respectively thereof. With this construction, blood and added fumarate solution flowing through the enzyme unit 7 must pass through the enzymic preparation 10 in direct contact therewith.

Figure 3:
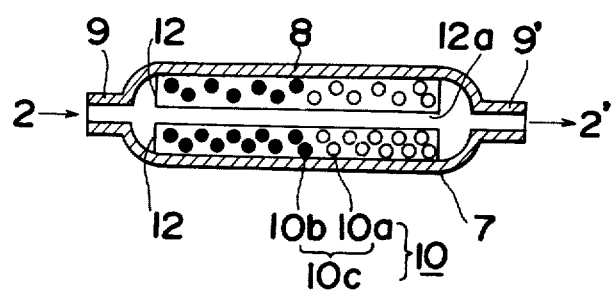
FIG. 3 is an enlarged cross-sectional view of another type of enzyme unit employable in the purification means of FIG. 1.

Alternatively, as shown in FIG. 3, the enzymic preparation 10 may be formed on the inner wall of an open-ended tube 12, which is fitted in the main portion 8, and defines a hollow central portion 12a through which blood and added fumarate solution may flow, while in contact with the enzymic preparation 10.

The general method of preparation of the enzymic preparation 10, specific examples of whose composition and preparation will be given later is as follows. A polymer incorporating an enzyme E is produced by polymerization of an acrylamide monomer, for example acrylamide, or N, N' methylenebisacrylamide, in a solution containing the enzyme E, and the polymer thus produced is then formed into grains. Alternatively the preparation 10 may be constituted by a plurality of semipermeable microcapsules, of nylon, polyurea, or material with similar qualities, which contain the enzyme E. In another method of preparation, first an enzyme which is insoluble, i.e., insoluble in water, is produced by bonding the enzyme E to an insoluble carrier, which may be, for example, activated charcoal, kaolinite, an ion-exchange resin such as a decolorization ion-exchange resin, DEAE cellulose, or DEAE Sephadex, a reactive polysaccharide such as carboxy methyl dextran azid, p-aminobenzyl cellulose azid, or bromoacetyl cellulose, or a reactive high molecular substance such as diazonium salt of γ-p-aminobenzoyl amidopropylsilane glass, diazonium salt of p-aminophenylalanine and amino acid (i.e., glycine, leucine, alanine) copolymer. The insoluble enzyme thus produced is incorporated to form a bonding lattice in an acrylamide polymer and subsequently formed into grains, or is employed in the production of semipermeable microcapsules in the manner referred to above.

To form a tubular enzyme unit 7 such as shown in FIG. 3, a polymer incorporating the enzyme E is formed by polymerization of an acrylamide monomer such as noted above, this polymer being formed in an open-ended tube in which there is held a rod extending along the tube longitudinal axis, and one end of which is closed during polymerization process by a stopper, the stopper and rod being removed when the polymer reaches a gel state.

The enzyme E employed as the enzymic preparation 10 may be one or several kinds of enzyme, which are selected in accordance with the type of treatment with which the blood purification means is associated. If, for example, the blood purification means is used in treatment of a patient who is suffering from a liver disorder, and from whose blood it is required to remove ammonia, the enzyme E is suitably aspartase, thereby being produced an aspartase preparation 10a, and the blood purification means functions as follows. Blood is led from the patient along the outflow cannula 2, into which controlled amounts of fumarate solution also are supplied from the reservoir 3 by the supply means 4, the amount of fumarate solution thus supplied being determined in reference to the amount of ammonia in the patient's blood, which is metered by conventionally known means not shown. The blood now containing an addition of fumarate solution is led into the enzyme unit 7, wherein the blood and added fumarate come into contact with the enzymic preparation 10a, either while flowing directly through the preparation 10a, as in the unit of FIG. 2, or while flowing through the tube central portion 12a, as in the unit of FIG. 3, and the aspartase preparation 10a catalyzes a reaction of fumaric acid and ammonia to aspartic acid, which is non toxic to the patient, blood returned to the patient along the inflow cannula 2' thus having ammonia specifically removed therefrom, but other required substances being left in the blood.

If the blood purification means is employed in treatment of a patient suffering from leukemia, and it is required to selectively remove asparagine from the patient's blood, there may be suitably employed three types of enzyme E, these types being aspartase preparation 10a, asparaginase preparation 10b, and aspartase-asparaginase preparation 10c, the aspartase and asparaginase being mixed at the start of preparation and then together incorporated in a polymer, or being provided as individual grains, or microcapsules which are subsequently mixed. The aspartase preparation 10a is suitably provided at outlet side 9' of the unit 7, and the preparation 10 at inlet side 9 of the unit 7 may be constituted by asparaginase preparation 10b or by aspartase-asparaginase preparation 10c. Amount of fumarate added is varied in accordance with the concentration of asparagine in the patient's blood, and is generally made such that the concentration of fumaric acid in the outflow cannula 2 is of the order of $10^{-5}$ M to $10^{-3}$ M. In enzyme unit 7, the fumarate solution and asparagine first contact with the asparaginase preparation 10b, or aspartase-asparaginase preparation 10c and then with the aspartase preparation 10a. By the action of the asparaginase portion of the preparation 10 the asparagine is decomposed to aspartic acid and ammonia, and by the action of the aspartase portion of the preparation 10 the ammonia produced combines with fumaric acid to form aspartic acid, blood returned along the inflow cannula 2' thus being cleaned both of asparagine and of ammonia produced due to elimination of asparagine.

A favourable temperature for the reactions described above is about 37°C, and to maintain this temperature this embodiment of the invention and other embodiments thereof described below are suitably enclosed in a constant-temperature cabinet, or associated with other conventionally known temperature-control means not shown.

Figure 4:
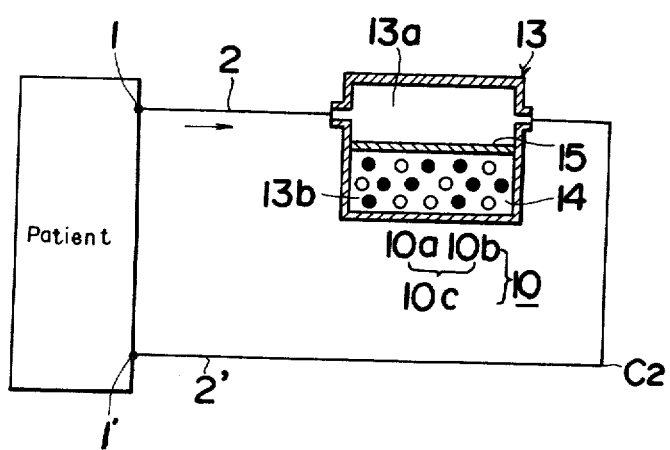
FIG. 4 is a schematic lay-out view of a blood purification means according to a second embodiment of the invention.

Referring now to FIG. 4, there is shown another embodiment of the invention wherein the outflow cannula 2 and inflow cannula 2' from part of a circuit C2 and respectively carry blood of a patient being treated into and from a hemodialysis unit 13, which has two main compartments 13a and 13b separated by a semipermeable membrane 15 made of cellophane or cuprophane, for example. Blood of the patient is led into and from the compartment 13a, and the compartment 13b holds a dialysate 14 which contains additions of fumarate and an enzymic preparation 10. To prevent coagulation of blood flowing through the circuit C2, heparin or other suitable anticoagulant may be supplied into the outflow cannula 2 at a suitable point. Also there may be provided on the circuit C2 a pump to maintain flow of blood around the circuit, not shown.

The enzymic preparation 10 is mainly an aspartase composition if purification of blood of a patient suffering from liver disorder is to be effected, and has a mixed aspartase and asparaginase composition if the purification means is used in treatment of leukemia. Most suitably the enzymic preparation is in a water soluble, but may also be prepared as grains or microcapsules of aspartase preparation 10a, asparaginase preparation 10b, or aspartase-asparaginase preparation 10c in the manner described above in reference to the first embodiment. In the case of a patient being treated for a liver disorder, simultaneously with conventional dialysis of the patient's blood in the homodialysis unit 13. By the action of the aspartase preparation 10a in the dialysate 14, ammonia which has diffused through the membrane 15 combine with fumaric acid, which is also in the dialysate 14, to form aspartic acid. In treatment of leukemia simultaneously with hemodialysis of a patient's blood, asparagine entering the dialysate 14 is converted to aspartic acid and ammonia by the action of the asparaginase portion of the enzymic preparation 10', after which the ammonia thus produced combines with fumaric acid to form aspartic acid by the action of the aspartase portion of the preparation 10'.

FIG. 5 shows a further embodiment of the invention according to which in association with a circuit C2 including an outflow cannula 2, inflow cannula 2', and hemodialysis unit 13, there is constituted a circuit C3 comprising a tract 16 which leads from the dialysate compartment 13b of the hemodialysis unit 13 into a compartment 17a of a dialyzer 17, which comprises two main compartments 17a and 17b separated by a semipermeable membrane 18, and then from the dialyzer compartment 17a back to the dialysate compartment 13b of the hemodialysis unit 13 through the tract 16. Dialysate employed in the hemodialysis unit 13 is continuously driven around the circuit C3 by a pump 21, which is provided at a suitable location on the tract 16, for example on the dialysate outlet side of the dialysate compartment 13b. Whereas the semipermeable membrane of the hemodialysis unit 13 is a membrane such as cellophane or cuprophane, or other material normally employed in hemodialysis equipment, the semipermeable membrane 18 of the dialyzer 17 is a membrane which may serve in dialysis of low molecular substances, and which permits diffusion therethrough of ammonia molecules, but not of aspartic acid molecules, a suitable material being for example hollow fibre unit 6/HFO-1 (a trademark owned by Dow Chemical Ltd.). There is also preferably provided means, not shown, for supplying suitable quantities of heparin or other anticoagulant into the outflow cannula 2, and pump means for maintaining flow of blood in the circuit C2.

Figure 5A:
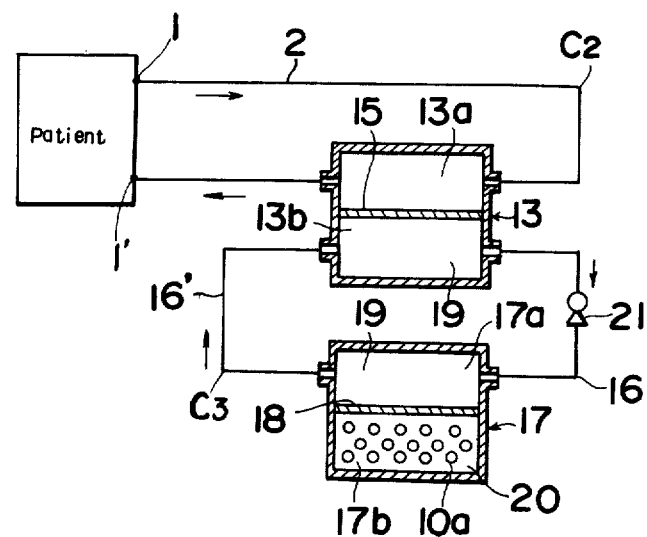
FIGS. 5(a) and 5(b) are schematic lay-out views of a blood purification means according to a third embodiment of the invention.

Referring more particularly to FIG. 5(a), if the purification means is employed in treatment of liver disorder, the dialysate compartment 13b of the hemodialysis unit 13 contains dialysate 19, which has a composition such as normally employed in hemodialysis, and the compartment 17b of the dialyzer 17 contains a dialysate 20 to which has been added fumarate and aspartase preparation 10a prepared in the manner described above. During dialysis of a patient's blood in the hemodialysis unit 13 ammonia diffuses from the blood into the dialysate 19 and is carried together with the dialysate 19 along the tract 16 into the compartment 17a of the dialyzer 17, from which it diffuses into the dialyzer compartment 17b, where, by the action of the aspartase preparation 10a it is converted to aspartic acid, which is unable to pass through the semipermeable membrane 18 into the dialyzer compartment 17a, the embodiment of FIG. 5 thus presenting the advantage of reduction of transport of aspartic acid into the blood stream of a patient.

Figure 5B:
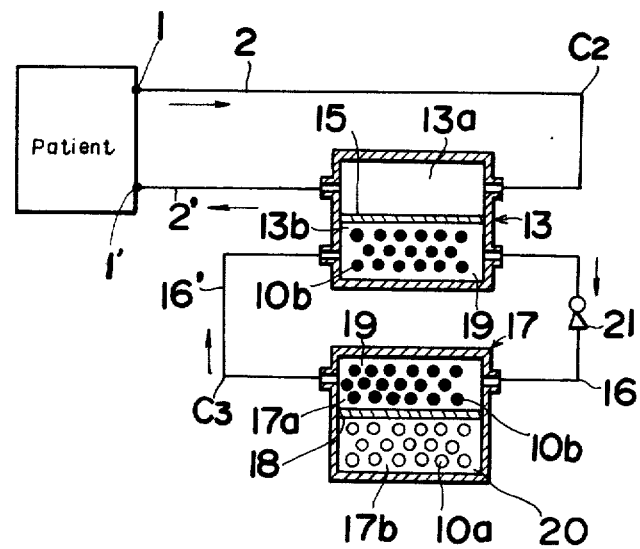

In FIG. 5(b), in treatment of leukemia the dialyzer 17 employs a dialysate 20 containing additions of fumarate and aspartase preparation 10a, as before, and the hemodialysis unit 13 employs a dialysate 19 which includes an addition of an asparaginase preparation 10b. In this case, asparagine in blood led into the hemodialysis unit 13 diffuses into the dialysate 19, and there decomposed into aspartic acid and ammonia by the action of the asparaginase preparation 10b, the ammonia thus produced being carried to the dialyzer 17, where it diffuses into the dialyzate 20 and is converted into aspartic acid, which is retained in the dialyzer compartment 17b, as described above.

Thus, by employment of a suitably prepared enzyme, which is highly selective in its action, the invention provides a blood purification means permitting removal of an unrequired substance from the blood of a patient, while allowing other, required substances to remain in the blood.

Specific examples of composition and preparation of the enzyme preparation employed in the means of the invention include the following. In the examples below the term 'unit' is in reference to activity of an enzyme. In the case of aspartase, the enzyme reaction was carried out at 37°C using ammonium fumarate (pH 8.5) as a substrate, and L-aspartic acid produced was determined by Folin's colorimetric method. One unit is defined as the quality of enzyme which will catalyze the production of one micromol of L-aspartic acid per one hour. In the case of asparaginase, the enzyme reaction was carried out at 37°C using L-asparagine (pH 8.0) as a substrate, and liberated ammonia was measured by Nessler's colorimetric method. One unit is defined as the quality of enzyme which will catalyze the liveration of one micromole of ammonia per one minute.

EXAMPLE 1

100 mg of crude aspartase (60 units/mg) obtained from Escherichia coli are dissolved in 20 ml of water. An addition of 6 ml of triethylamino ethylcelluslose of OH type is made to this solution, which is then stirred for 1 hour at 23°C. After this the solution is filtered, and the residue is washed with water, thereby being obtained 3 g of insoluble aspartase (400 units/g). This insoluble aspartase is suspended in a 0.05 M phosphate buffer solution (pH is 7.0), containing 1.5 g of acrylamide and 0.08 g of N, N-methylenebisacrylamide, and to which was further added 1 ml of 5 percent β-dimethylaminopropionitrile and 1 ml of 1 percent potassium persulfate. This solution is maintained at 23°C for 30 minutes, and thereby being obtained 14 g of immobilized aspartase preparation (77 units/g), which is pulverized to produce grains having a size of 30 – 100 mesh.

EXAMPLE 2

20 mg of partially purified aspartase (600 units/mg) obtained from Escherichia coli is dissolved in 10 ml of water. 6 ml of diethylaminoethyl-Sephadex (Cl-type) is added to this solution, which is then stirred for 1 hour at 23°C. After this the solution is filtered, the residue obtained is thoroughly washed with water, and thereby being obtained 3 g of insoluble aspartase (800 units/g). This insoluble aspartase is suspended in 15 ml of 0.05 M phosphate buffer solurtion (pH 8.5) containing 4 millimole of 1,6 hexamethylene diamine, the suspension thus formed being then dispersed in 100 ml of medium constituted by cyclohexane and choroform in a 5:1 ratio. This liquid dispersion medium is then brought to 4°C, and 75 ml of an organic mixture solvent described above containing 7 millimole of 2,4-toluene di-isocyanate is added thereto. This mixture is stirred for 3 minutes at 4°C, and polyurea microcapsules containing aspartase is produced. After separation by filtration, these microcapsules are washed with ethanol and water, the final product obtained being 25 g of microcapsulated aspartase preparation (67 units/g) having a particle diameter of 200 – 500 microns.

EXAMPLE 3

100 mg of crude aspartase (60 units/mg) obtained from Escherichia coli is dissolved in 20 ml of water, after which 6 ml of calcium phosphate gel is added and the solution is stirred for one hour at 23°C. After this, the precipitation is separated by centrifuging, and then thoroughly washed with water, there thus being obtained 4 g of insoluble aspartase (150 units/g). Subsequent procedure is as described in Example 1, the final product being 14.3 g of immobilized aspartase preparation (21 units/g).

EXAMPLE 4

10 mg of partially purified asparaginase (70 units/mg) obtained from Proteous vulgaris, 0.75 g of acrylamide, 0.04 g of N, N'-methylenebisacrylamide, and 300 mg of L-sodium aspartate are dissolved in 4 ml of 0.1 M phosphate buffer solution (pH 7.0). To this solution 0.5 ml of 1 percent dimethylaminopropionitrile and 0.5 ml of 1 percent potassium persulfate are added, and then polymerization is allowed to proceed for 30 minutes at 23°C, thereby producing 7 g (wet weight) of immobilized asparaginase preparation (50 units/g), which is then pulverized to produce grains having a size of 30 – 100 mesh.

EXAMPLE 5

0.1 mg of crystalline asparaginase (300 units/mg) obtained from Proteus vulgaris and 300 mg of L-sodium aspartate are dissolved in 2 ml of 0.1 M phosphate buffer (pH 7.0). To this solution 1 ml of 75 percent acrylamide solution and 1 ml of 4 percent N, N' methylenebisacrylamide solution are added. The temperature of the mixture is brought to 4°C, and 0.5 ml of 2.5 percent potassium persulfate solution and 0.5 ml of 5 percent β-dimethylaminopropionitrile solution are added. 1.2 ml of this reaction mixture is then poured into an open-ended glass tube, which is held vertically and has an inner diameter of 5 mm and a length of 15 cm, and the lower end of which is sealed by a stopper. A glass rod, which has a diameter of 3 mm and has been coated with a non-ionic surfactant such as TL-10, is vertically inserted, in a central position of tube. The polymerization is completed at 23°C for about 5 minutes. After which the rod and stopper are removed, and the gel is thoroughly washed with water. There is thus produced an asparaginase tube, other tubes being produced in the same manner.

Although the present invention has been fully described in conjunction with the preferred embodiments thereof with reference to the accompanying drawings, various changes and modifications are apparent to those skilled in the art.

Therefore, these changes and modifications should, unless otherwise they depart from the true scope of the present invention, be construed as included therein.

What is claimed is:

1. A blood purification means comprising
   a first cannula circuit for transport of blood having both ends which are adapted to be connected to the blood stream of a patient to be treated,
   a hemodialysis unit having a first dialysate provided in said first circuit, the first dialysate being effected with the blood of said first cannula circuit through a semi-permeable membrane, a second cannula circuit for transport of the first dialysate of said hemodialysis unit having both ends connected to said hemodialysis unit, a dialyzer having a second dialysate provided in said second cannula circuit, the second dialysate containing additions of fumarate and an aspartase preparation and being selectively effected with said first dialysate through a semipermeable membrane which permits diffusion therethrough of ammonia molecules, but not of aspartic acid molecules, and a pump for driving said first dialysate around said second cannula circuit.

2. A blood purification means comprising a first cannula circuit for transport of blood having both ends which are adapted to be connected to the blood stream of a patient to be treated, a hemodialysis unit having a first dialysate provided in said first circuit, the first dialysate containing an asparaginase preparation and being effected with the blood of said first cannula circuit through a semipermeable membrane.

a second cannula circuit for transport of the first dialysate of said hemodialysis unit having both ends connected to said hemodialysis unit, a dialyzer having a second dialysate provided in said second cannula, the second dialysate containing additions of fumarate and an asparaginase preparation and being selectively effected with said first dialysate through a semipermeable membrane which permits diffusion therethrough of ammonia molecules, but not of aspartic acid molecules, and a pump for driving said first dialysate around said second cannula circuit.

* * * * *